US010747850B2

(12) United States Patent
Ashoori et al.

(10) Patent No.: US 10,747,850 B2
(45) Date of Patent: Aug. 18, 2020

(54) MEDICATION SCHEDULING AND ALERTS

(71) Applicant: INTERNATIONAL BUSINESS MACHINES CORPORATION, Armonk, NY (US)

(72) Inventors: Maryam Ashoori, White Plains, NY (US); Benjamin D. Briggs, Waterford, NY (US); Lawrence A. Clevenger, Rhinebeck, NY (US); Leigh Anne H. Clevenger, Rhinebeck, NY (US); Jonathan H. Connell, II, Cortlandt-Manor, NY (US); Nalini K. Ratha, White Plains, NY (US); Michael Rizzolo, Albany, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 769 days.

(21) Appl. No.: 15/083,960

(22) Filed: Mar. 29, 2016

(65) Prior Publication Data
US 2017/0286632 A1 Oct. 5, 2017

(51) Int. Cl.
*G06F 19/00* (2018.01)
*G16H 10/60* (2018.01)

(52) U.S. Cl.
CPC ........ *G06F 19/3456* (2013.01); *G06F 19/326* (2013.01); *G16H 10/60* (2018.01)

(58) Field of Classification Search
None
See application file for complete search history.

(56) References Cited

U.S. PATENT DOCUMENTS

| 8,708,903 | B2 | 4/2014 | Tran | |
|---|---|---|---|---|
| 8,731,512 | B2 | 5/2014 | Borras et al. | |
| 8,762,166 | B2 | 6/2014 | Inciardi et al. | |
| 2004/0133543 | A1* | 7/2004 | Shlaes | G06F 16/25 |
| 2007/0083396 | A1* | 4/2007 | Kanada | G06F 19/321 |
| | | | | 705/3 |
| 2008/0195594 | A1* | 8/2008 | Gerjets | G16H 50/20 |
| 2009/0326509 | A1 | 12/2009 | Muse et al. | |
| 2010/0198755 | A1* | 8/2010 | Soll | G06F 19/324 |
| | | | | 706/11 |

(Continued)

OTHER PUBLICATIONS

Garcia-Ceja, Enrique, et al. "Long-Term Activity Recognition from Wristwatch Accelerometer Data," Sensors, 2014, www.mdpi.com/journal/sensors, pp. 22500-22524.

(Continued)

*Primary Examiner* — Michael Tomaszewski
*Assistant Examiner* — Jay M. Patel
(74) *Attorney, Agent, or Firm* — Cantor Colburn LLP; Anthony Curro

(57) ABSTRACT

Embodiments include method, systems and computer program products for providing medication-related feedback. Aspects include receiving medication information for a patient. Aspects also include receiving a biological, behavioral, or environmental output from a sensor. Aspects also include determining, based upon the biological, behavioral, or environmental output and the medication information for the patient, whether a medication dose is needed. Aspects also include, based on a determination that the medication dose is needed, generating an alert.

18 Claims, 5 Drawing Sheets

(56) References Cited

U.S. PATENT DOCUMENTS

| | | | | |
|---|---|---|---|---|
| 2010/0204920 | A1* | 8/2010 | Dranitsaris | G06F 19/00 702/19 |
| 2010/0274584 | A1* | 10/2010 | Kim | G06Q 50/24 705/3 |
| 2011/0077973 | A1* | 3/2011 | Breitenstein | G06Q 10/10 705/3 |
| 2011/0208437 | A1* | 8/2011 | Teicher | A61B 5/024 702/19 |
| 2011/0238439 | A1* | 9/2011 | Rice | G06F 19/325 705/2 |
| 2012/0010900 | A1* | 1/2012 | Kaniadakis | G06F 19/328 705/2 |
| 2012/0025964 | A1* | 2/2012 | Beggs | B60Q 1/2673 340/435 |
| 2012/0110016 | A1* | 5/2012 | Phillips | G06Q 10/06 707/780 |
| 2013/0226608 | A1* | 8/2013 | Di Lascia | G16H 50/30 705/2 |
| 2013/0262155 | A1* | 10/2013 | Hinkamp | G06Q 40/08 705/4 |
| 2014/0095201 | A1* | 4/2014 | Farooq | G16H 50/30 705/3 |
| 2014/0139665 | A1* | 5/2014 | Pinapala Venkata | H04M 1/72522 348/143 |
| 2014/0172572 | A1* | 6/2014 | Akin | G06Q 30/0261 705/14.58 |
| 2014/0236630 | A1* | 8/2014 | Murata | G06Q 10/06398 705/3 |
| 2014/0278475 | A1* | 9/2014 | Tran | G06F 19/3418 705/2 |
| 2015/0006192 | A1* | 1/2015 | Sudharsan | G06N 5/048 705/2 |
| 2015/0012295 | A1* | 1/2015 | Mahoney | G06F 19/3475 705/3 |
| 2015/0112208 | A1 | 1/2015 | He et al. | |
| 2015/0095016 | A1* | 4/2015 | Karres | G06F 19/00 704/9 |
| 2015/0223705 | A1 | 8/2015 | Sadhu | |
| 2015/0278475 | A1 | 10/2015 | Shor | |
| 2015/0339460 | A1 | 11/2015 | Marsico | |
| 2015/0363563 | A1* | 12/2015 | Hallwachs | G06F 19/321 705/3 |
| 2016/0009175 | A1* | 1/2016 | McNew | G01C 21/365 340/438 |
| 2016/0061625 | A1* | 3/2016 | Wang | G06Q 30/0214 701/454 |
| 2016/0063209 | A1* | 3/2016 | Malaviya | G16H 50/50 706/12 |
| 2017/0116388 | A1* | 4/2017 | Robinson | G06F 40/205 |
| 2017/0124284 | A1* | 5/2017 | McCullough | A61M 5/158 |

OTHER PUBLICATIONS

Johnston, Andrew H. et al. "Smartwatch-Based Biometric Gait Recognition," Department of Computer and Information Science, WISDM Laboratory Fordham University, Bronx NY 10458, pp. 1-6.

Rosner, David et al., "Wearable Medication Reminder Architecture Enhancement," 2015 20th International Conference on Control Systems and Science, Jun. 2015, pp. 279-284.

* cited by examiner

MEDICATION SCHEDULING AND ALERTS

BACKGROUND

The present disclosure relates generally to providing medication-related feedback, and more specifically to methods, systems and computer program products for recommending medication scheduling and sending alerts based upon continuous monitoring of biological, behavioral, or environmental sensor output.

Many people have trouble identifying what medication to take and at what time based upon medication labeling or even based upon a doctor's prescription and advice. People are frequently concerned about whether certain physiological side effects or conditions warrant a change or adjustment in their medication timing or dosage. The difficulty that individual patients experience in assessing their own medication routine can further be compounded when patients take multiple medications or when the patients' judgment is clouded, for example by pain or the effects of various medications.

Such difficulties in self-assessing medication scheduling and dosages and physiological symptoms can result in over-medication or under-medication, and could lead to potentially life-threatening situations. For example, failure to recognize reduction in blood pressure could lead to over consumption of blood pressure medication. In contrast, failure to recognize elevation of blood pressure could result in potentially serious complications if the appropriate time for taking a blood pressure medication is missed. Moreover, a patient's inability to recognize symptoms of an allergic reaction that should call for an adjustment in medication could lead to serious problems that require emergency medical intervention.

SUMMARY

In accordance with an embodiment, a computer-implemented method for providing medication feedback is provided. The method includes receiving medication information for a patient. The method also includes receiving a biological, behavioral, or environmental output from a sensor. The method also includes determining, based upon the biological, behavioral, or environmental output and the medication information for the patient, whether a medication dose is needed. The method also includes, based on a determination that the medication dose is needed, generating an alert.

In accordance with another embodiment, a computer program product for providing medication feedback is provided. The computer program product includes a computer readable storage medium having program instructions embodied therewith, the program instructions executable by a processor to cause the processor to receive medication information for a patient. The processor is also configured to receive biological, behavioral, or environmental output from a sensor. The processor is also configured to determine, based upon the biological, behavioral, or environmental output and the medication information for the patient, whether a medication dose is needed. The processor is also configured to, based upon a determination that the medication dose is needed, generate an alert.

In accordance with a further embodiment, a processing system for providing medication feedback includes a processor in communication with one or more types of memory. The processor is configured to receive medication information for a patient. The processor is also configured to receive a biological, behavioral, or environmental output from a sensor. The processor is also configured to determine, based upon the biological, behavioral, or environmental output and the medication information for the patient, whether a medication dose is needed. The processor is also configured to, based on a determination that the medication dose is needed, generate an alert.

BRIEF DESCRIPTION OF THE DRAWINGS

The subject matter of the present disclosure is particularly pointed out and distinctly claimed in the claims at the conclusion of the specification. The foregoing and other features and advantages of the one or more embodiments disclosed herein are apparent from the following detailed description taken in conjunction with the accompanying drawings in which:

DETAILED DESCRIPTION

Figure 1:
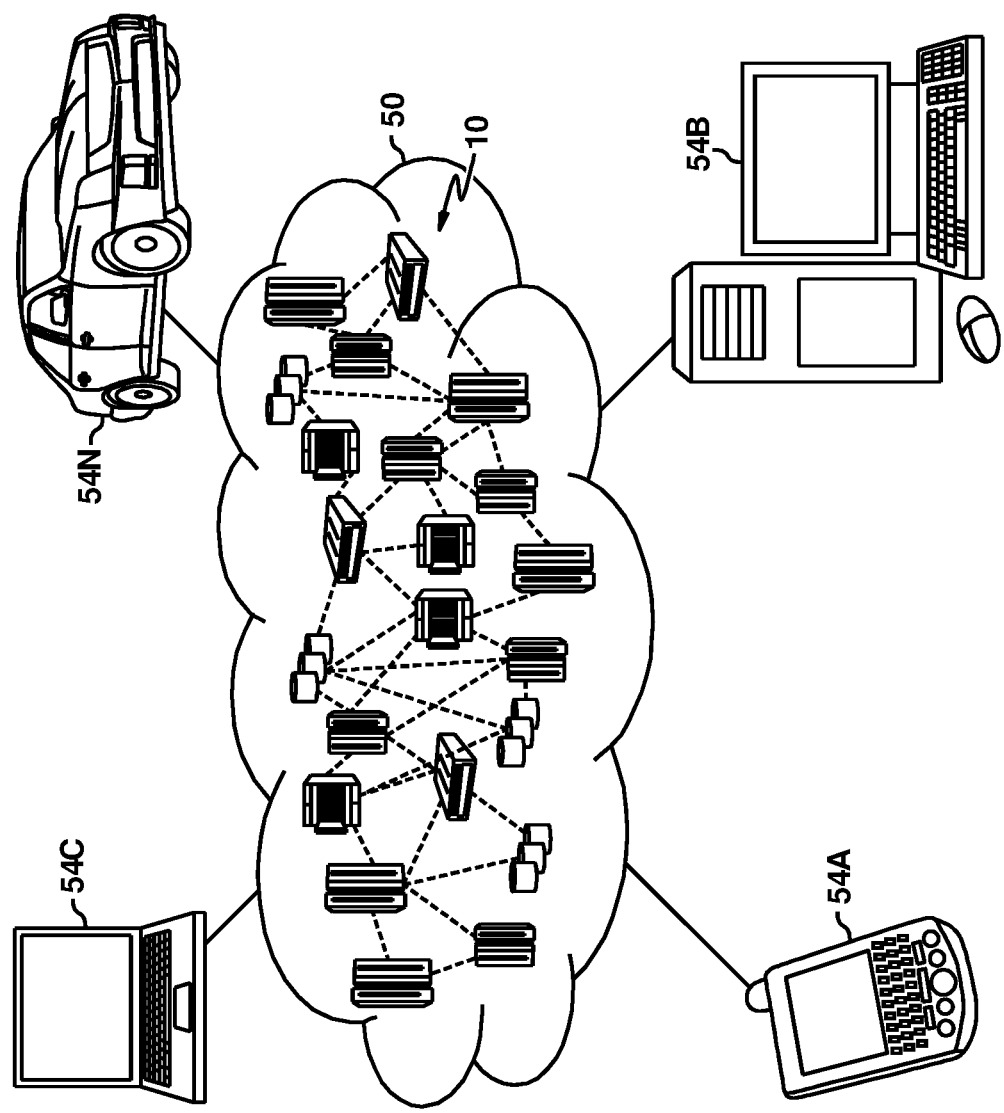
FIG. 1 depicts a cloud computing environment according to an embodiment of the present invention.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
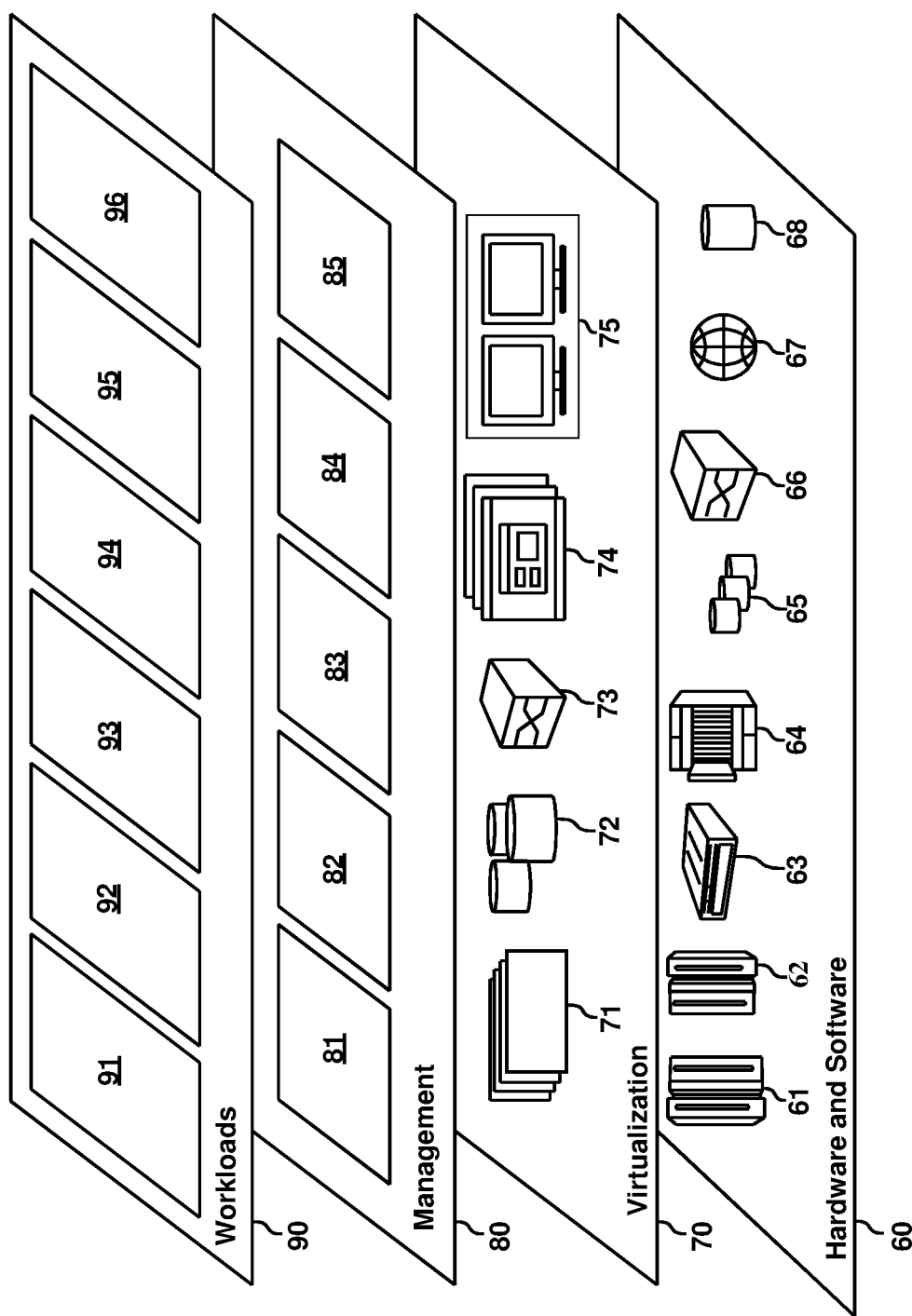
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and image processing 96.

In accordance with one or more embodiments of the disclosure, methods, systems and computer program products for providing medication-related feedback are provided.

Figure 3:
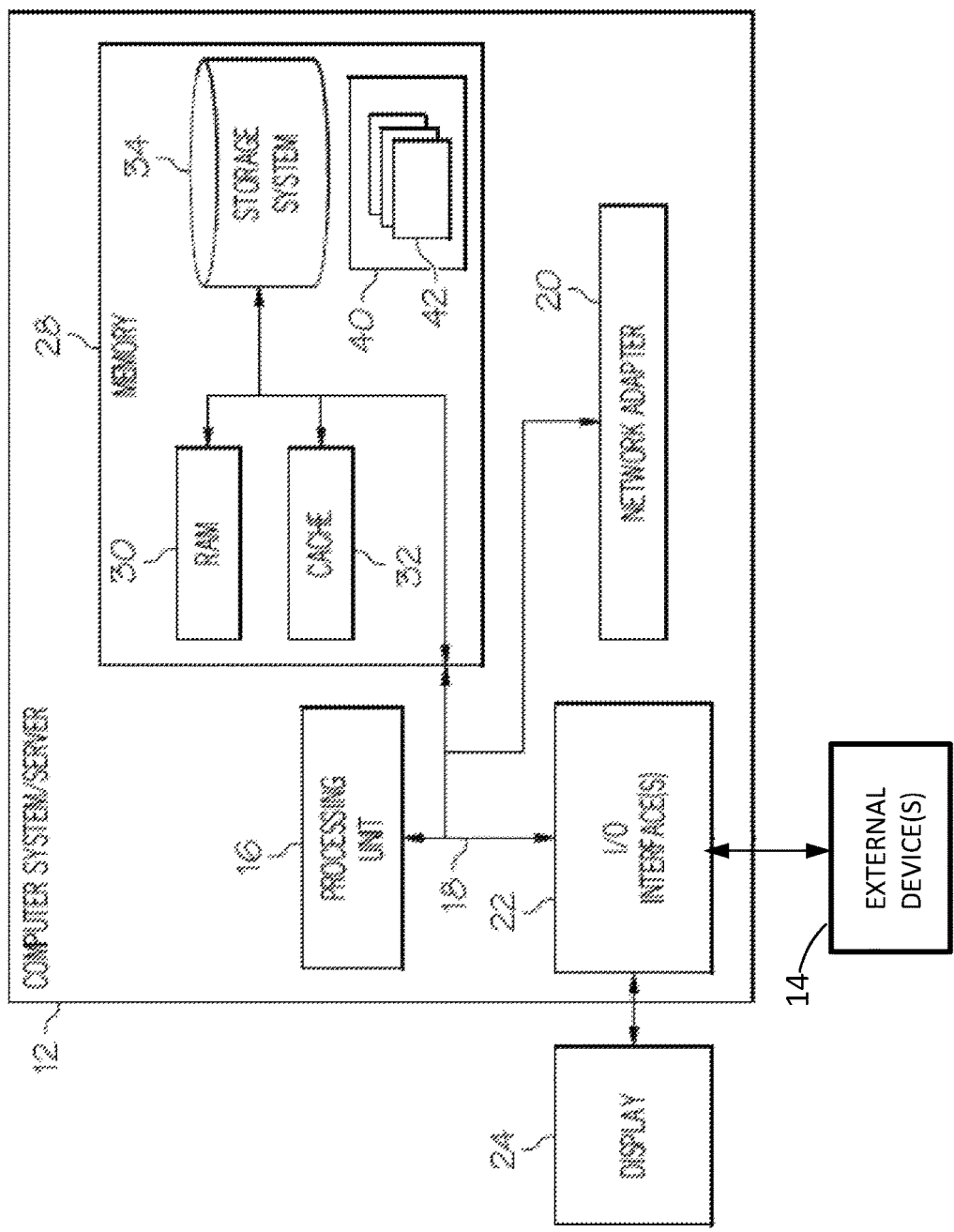
FIG. 3 is a computer system according to one or more embodiments.

Referring now to FIG. 3, a schematic of a cloud computing node 100 included in a distributed cloud environment or cloud service network is shown according to a non-limiting embodiment. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 in cloud computing node 100 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of the present disclosure, one or more embodiments provide systems and methodologies for providing medication-related feedback based upon medication information from a patient and biological output. More specifically, the present disclosure provides a recommendation for an optimum schedule for taking or discontinuing medications, monitoring potential side effects, and providing alerts if needed. More specifically, the systems and methodologies for recommending medication scheduling and sending alerts are based on continuous monitoring of vital signs.

Figure 4:
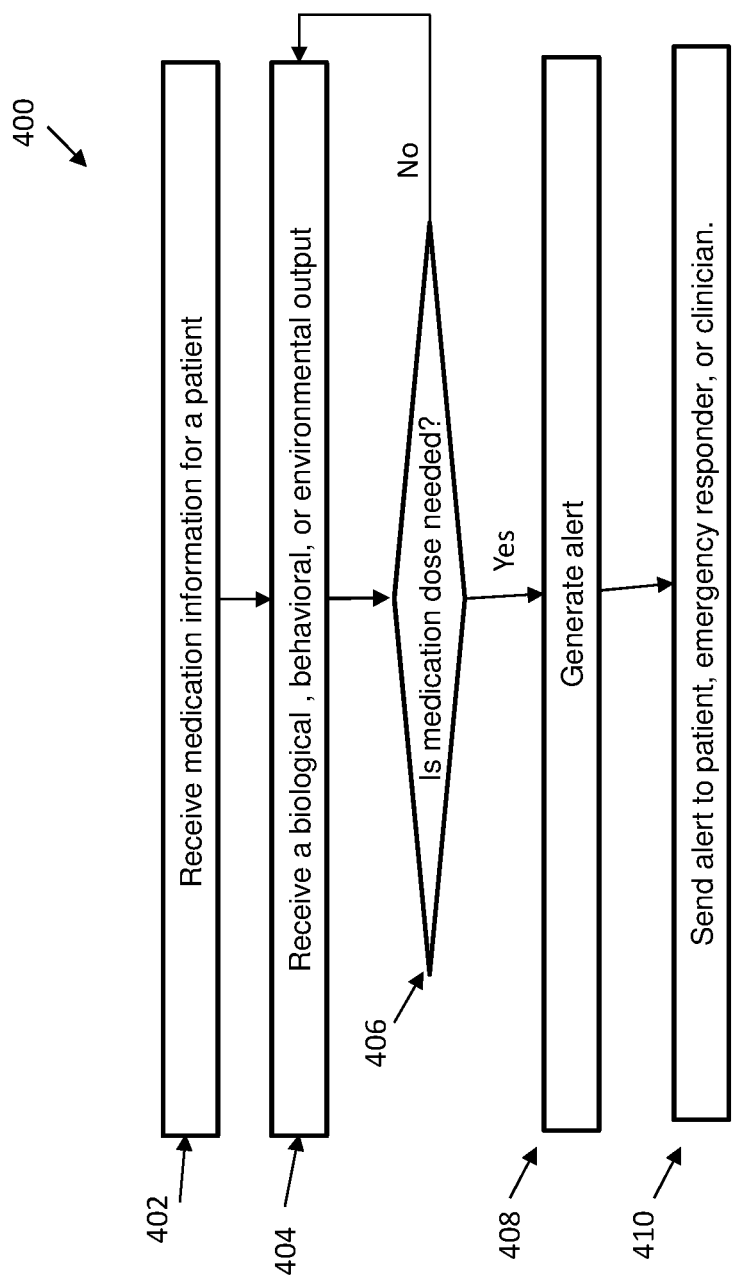
FIG. 4 is a flow diagram illustrating a method for providing medication-related feedback according to one or more embodiments.

Referring now to FIG. 4, a flow chart illustrating a method 400 for providing medication-related feedback. As shown at block 402, according to one or more embodiments, the method 400 includes receiving medication information from a patient. The method 400 also includes, as shown at block 404, receiving an output, including a biological, behavioral, and/or environmental output. In some embodiments, the method includes receiving biological output. In some embodiments, the method includes receiving behavioral output. In some embodiments, the method includes receiving environmental output. Next, as shown at decision block 406, the method 400 considers whether medication is needed. The consideration of whether medication is needed can be based upon the medication information and the output. If medication is not needed, the method 400 can return to block 404. If medication is needed, the method 400 continues to block 408 and generates an alert. The method 400 next includes, as shown at block 410, sending an alert to a patient, an emergency responder or a clinician.

Medication information for a patient can be received in any manner. For example, medication information for a patient can be manually entered into a system or collected via other systems, such as collection from patient health records. Medication information for a patient can include, but is not limited to, medication identity, medication dose and/or dose scheduling, expected or potential side effects or adverse reactions, indications for a medication, and any other information related to a given medication available through public or private records. Medication information for a patient can include personalized patient data, such as a patient's medical history or data needed or desired for medication dosing, such as body weight, age, height, or gender.

In some embodiments, medication information for a patient is collected through a consumer device, such as a smart phone, smart watch, or laptop computer. In one embodiment, a patient's medical history is acquired from electronic medical records (EMRs) or electronic health records (EHRs).

Biological output includes any biological data that can affect a patient's health, aid in a diagnosis, or relate to medication scheduling or medication dosing. Biological data can include, for example, heart rate, heartbeat, heart intensity, blood glucose, temperature, blood pressure, respiration rate, hormonal or blood sugar levels, sodium levels, or body weight. The sensors can include wearable devices, such as heart rate monitors, body temperature sensors, blood oxygen sensors, breathing rate sensors, breathing volume sensors or EDA (electrodermal activity) sensors. In some embodiments, the sensors are included in wearable devices, such as consumer wearable devices. For example, the wearable devices can include smart watches, EKG devices, derma pads, pulse oximeters, chemical sensors, barometers, near field communication devices, respiratory monitors, accelerometers, heart rate sensors, global positioning devices, compasses or blood glucose monitors.

Behavioral output can include, for example, body movement patterns, mobility and/or motility measures, wakefulness, speech patterns, and the like.

Environmental output can include, for example, external temperature, location, humidity, pollen counts, radiation counts, air quality measures, and the like.

Output can be collected wirelessly or through a wired connection. Output can be transmitted to a processor wirelessly or through a wired connection. In some embodiments, output is collected at regular intervals. In preferred embodiments, output is collected continuously.

An alert can include information derived from the output and medication information for a patient. In some embodiments, an alert includes a recommended medication schedule. In some embodiments, an alert includes an instruction to take a medication. In some embodiments, an alert includes an instruction not to take a medication. An alert can include, for example, a recommended dosage and/or a time for a given medication. In some embodiments, an alert includes an identification of side effects or adverse reactions experienced by a patient. In some embodiments, the alert includes information concerning the severity of a side effect or adverse reaction. In some embodiments, an alert includes a call for emergency services.

Figure 5:
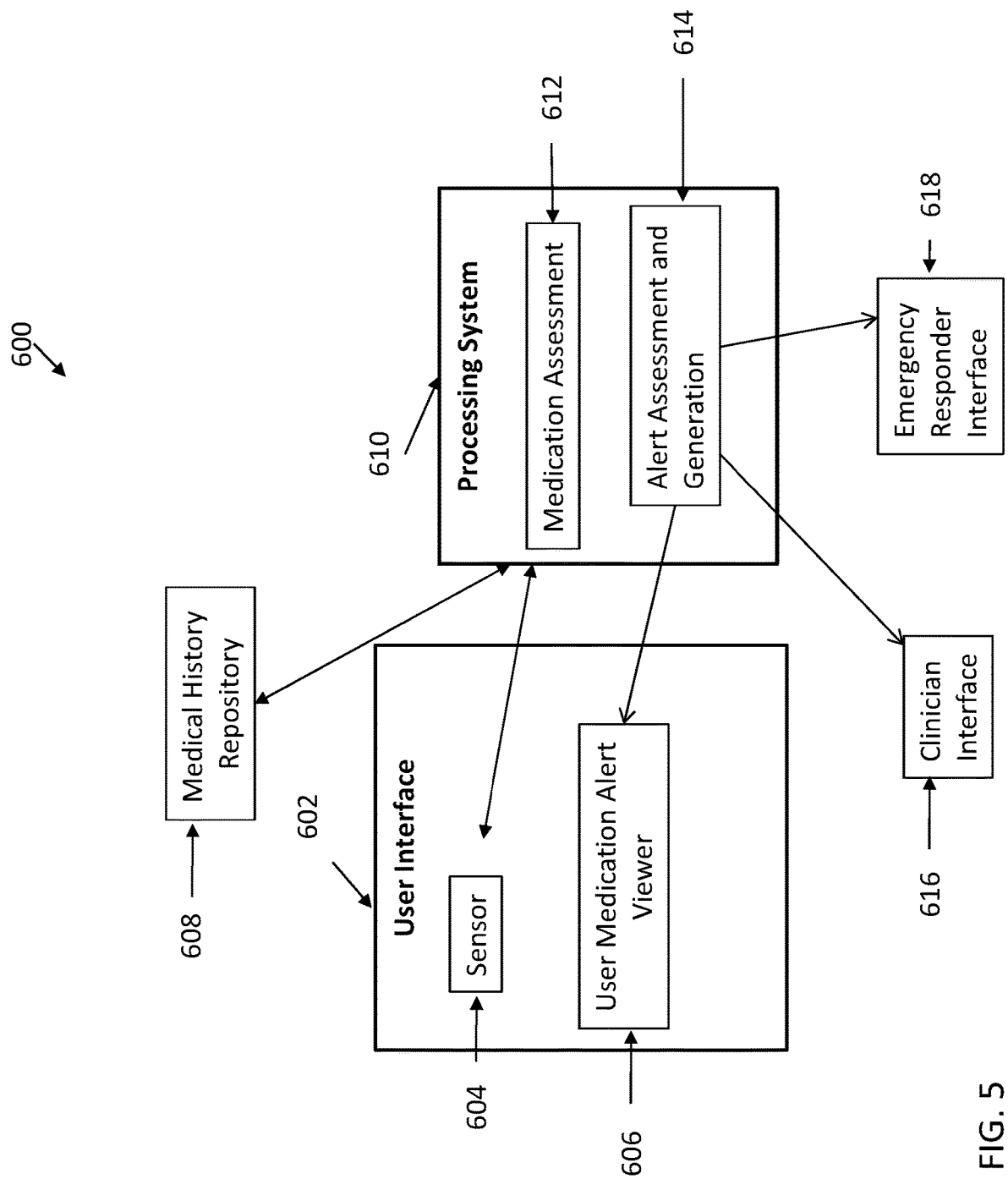
FIG. 5 is a block diagram illustrating a system for providing medication-related feedback according to one or more embodiments.

FIG. 5 depicts a block diagram illustrating an exemplary system 600 for providing medication feedback according to one or more embodiments. As is shown, the system 600 can include a user interface 602. The user interface 602 can include a sensor 604 and a user medication alert viewer 606. The user medication alert viewer 606, can be any component that enables a user to receive and interpret an alert. For example, the user medication alert viewer 606 can be a flat-panel display, an LED display, or an LCD display. In some embodiments, a user medication alert is output to a user at the user interface audibly in addition to or instead of a visually. Accordingly, in some embodiments, not shown, the user interface 602 includes an audio output. User interface interacts with processing system 610. As is shown, processing system 610 can provide a medication assessment 612. Medication assessment 612 can include, for example, an analysis of medications taken, dosages taken, expected side effects and biological responses, actual side effects and biological responses, and recommended dosing schedules. Medication assessment 612 can include a real time assessment of biometric data or a static assessment. Preferably, medication assessment 612 includes a real time assessment of biometric data. Processing system 610 also includes alert assessment and generation 614. Alert assessment and generation 614 can include determining whether to issue an alert, the contents of the alert, the format of the alert, and the recipient(s) of the alert. Alert assessment and generation 614 can interface with a clinician interface 616, emergency responder interface 618, and/or a user interface 602.

Thus, it can be seen from the forgoing detailed description that one or more embodiments of the present disclosure provide technical effects and benefits. The present disclosure provides a method for providing medication feedback based upon automated assessment of biological responses coupled with medication information, reducing or eliminating the confusion and ambiguity associated with self-assessment of symptomatology. For instance, in one or more embodiments, a patient can use a smartwatch to monitor symptoms and assess in real time whether to start or stop a given medication, potentially eliminating the need for a call to a medical professional and reducing the likelihood of under- or over-medication.

For example, a patient with an abnormal heart rhythm could be treated by a clinician with an antiarrhythmic medication. The patient can be instructed to take the medication when she feels improper beating of the heart. To assist in proper medication dosage, in accordance with the disclosure, a wearable device can monitor the patient's heart rate and blood oxygen level. When a pattern in heart rate and/or blood oxygen level changes, the system can send an alert to the patient with an instruction to take the antiarrhythmic medication.

For the same exemplary patient with an abnormal heart rhythm, a clinician may warn the patient of potential side effects of the medication and could instruct the patient to contact the clinician if certain symptoms are experienced, such as fainting, worsening arrhythmias, shortness of breath, abnormal heart rate, or cough. In accordance with the disclosure, a wearable device can continuously monitor the patient's heartbeat, breath, coughing, or whether fainting has occurred. Any of these occurrences can trigger an alert that can be sent directly to the clinician and emergency personnel.

The disclosure can provide continuous monitoring of side effects. For example, a patient could take a medication that makes him drowsy. In accordance with the disclosure, drowsiness can be detected on a wearable device by skin temperature and EDA sensors. Accelerometer sensors can detect lower than normal activity levels. When the patient enters his garage, his location could be recorded by GPS device and an RFID tag can indicate his presence in a vehicle. Systems of the disclosure can analyze the biometric output provided by the above-mentioned devices and generate an alert. For example, output to the patient can include haptic feedback (vibration), visual feedback and/or text messages indicating to the patient that he should not be driving in his current condition.

The disclosure can also aid in interpretation and analysis of drug interactions. For example, a patient can take a blood pressure medication in the morning that is known to have lesser effectiveness when taken with antacids. The patient could be concerned because she would like to take an antacid for upset stomach. The systems of the disclosure can provide personalized waiting times for taking an antacid that could be derived by learning through collection and accumulation of data pertaining to the patient. For instance, over the first few dosage administrations of the medication, the system could monitor the patient's blood pressure using a wearable sensor. Based on prior information, the system could provide an alert informing the patient of when to take the antacid.

The systems of the disclosure can advise of medications to discontinue. For example, for a patient with the flu, a physician could recommend taking ibuprofen every four hours until the fever dissipates. The physician could also recommend taking a cough suppressant every three hours for cough. The sensors on the wearable device can monitor body temperature (through a thermometer) and coughing (through a microphone). The system can regularly remind the patient to take the ibuprofen and cough suppressant. When the patient's temperature returns to normal, the system can generate an alert and notify the patient to stop taking ibuprofen.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting-data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for providing medication-related feedback, the method comprising:
   receiving, by a processor, medication information for a patient, the medication information comprising a potential side effect;
   continuously measuring in real-time, using a wearable device worn by the patient, a biological output of the patient, a behavioral output of the patient, and an environmental output, wherein the wearable device is configured to measure the biological output using an electrodermal activity sensor and a body temperature sensor, the wearable device is configured to measure the behavioral output using an accelerometer, and the wearable device is configured to measure the environmental output using an external temperature sensor, a global positioning device, a pollen count sensor, and an air quality sensor;
   receiving, by the processor, the biological output, the behavioral output, and the environmental output from the wearable device, the biological output comprising a biological response associated with the potential side effect, the behavioral output comprising a body movement pattern, and the environmental output comprising a location of the patient;
   determining, based upon the biological output, behavioral output, environmental output, and the medication information for the patient, whether a medication dose is needed, an actual side effect currently being experienced by the patient, and a severity of the side effect;
   based on a determination that the medication dose is needed and the severity of the side effect, generating an alert to take a medication;
   generating a location-specific warning to the patient based on the location and the severity of the actual side effect currently being experienced, wherein the location-specific warning comprises a message tailored to the location and the severity of the actual side effect; and
   transmitting the alert and the location-specific warning to one of the wearable device, a clinician interface, and an emergency responder interface.

2. The computer-implemented method of claim 1, wherein the medication information comprises an identity of a medication used by the patient, a medication dose used by the patient, and an administration time for the medication used by the patient.

3. The computer-implemented method of claim 1, wherein the wearable device is a smart watch.

4. The computer-implemented method of claim 1, wherein the biological output comprises a heart rate, a body temperature, a blood oxygen level, a breathing rate, an electrodermal activity, or a breathing volume.

5. The computer-implemented method of claim 1, wherein the biological output, behavioral output, or environmental output comprises real-time data.

6. The computer-implemented method of claim 1, wherein the alert comprises a recommendation to take a medication or to not take a medication.

7. The computer-implemented method of claim 4, wherein the alert comprises an emergency notification.

8. The computer-implemented method of claim 1, the method further comprising receiving, by the processor, a medical history of the patient.

9. The computer-implemented method of claim 1, further comprising sending the alert to the patient, an emergency responder, or a clinician.

10. The computer-implemented method of claim 1, wherein the alert comprises an observed side effect notification.

11. A computer program product for providing medication-related feedback, the computer program product comprising a computer readable storage medium having program instructions embodies therewith, the program instructions executable by a processor to cause the processor to:
   receive medication information for a patient, the medication information comprising a potential side effect;
   continuously measure in real-time, using a wearable device worn by the patient, a biological output of the patient, a behavioral output of the patient, and an environmental output, wherein the wearable device is configured to measure the biological output using an electrodermal activity sensor and a body temperature sensor, the wearable device is configured to measure the behavioral output using an accelerometer, and the wearable device is configured to measure the environmental output using an external temperature sensor, a global positioning device, a pollen count sensor, and an air quality sensor;
   receive the biological output, the behavioral output, and the environmental output from the wearable device, the biological output comprising a biological response associated with the potential side effect, the behavioral output comprising a body movement pattern, and the environmental output comprising a location of the patient;
   determine, based upon the biological output, behavioral output, environmental output, and the medication information for the patient, whether a medication dose is needed, an actual side effect currently being experienced by the patient, and a severity of the side effect;

based on a determination that the medication dose is needed and the severity of the side effect, generate an alert to take a medication;

generate a location-specific warning to the patient based on the location and the severity of the actual side effect currently being experienced, wherein the location-specific warning comprises a message tailored to the location and the severity of the actual side effect; and transmit the alert and the location-specific warning to one of the wearable device, a clinician interface, and an emergency responder interface.

12. The computer program product of claim 11, wherein the biological output, behavioral output, or environmental output comprises real-time data.

13. The computer program product of claim 11, wherein the alert comprises a recommendation to take a medication or to not take a medication.

14. A processing system for providing medication-related feedback, the processor system comprising:

a processor in communication with one or more types of memory, the processor configured to:

receive medication information for a patient, the medication information comprising a potential side effect;

continuously measure in real-time, using a wearable device worn by the patient, a biological output of the patient, a behavioral output of the patient, and an environmental output, wherein the wearable device is configured to measure the biological output using an electrodermal activity sensor and a body temperature sensor, the wearable device is configured to measure the behavioral output using an accelerometer, and the wearable device is configured to measure the environmental output using an external temperature sensor, a global positioning device, a pollen count sensor, and an air quality sensor;

receive the biological output, the behavioral output, and the environmental output from the wearable device, the biological output comprising a biological response associated with the potential side effect, the behavioral output comprising a body movement pattern, and the environmental output comprising a location of the patient;

determine, based upon the biological output, behavioral output, environmental output, and the medication information for the patient, whether a medication dose is needed, an actual side effect currently being experienced by the patient, and a severity of the side effect;

based on a determination that the medication dose is needed and the severity of the side effect, generate an alert to take a medication;

generate a location-specific warning to the patient based on the location and the severity of the actual side effect currently being experienced, wherein the location-specific warning comprises a message tailored to the location and the severity of the actual side effect; and transmit the alert and the location-specific warning to one of the wearable device, a clinician interface, and an emergency responder interface.

15. The processing system of claim 14, wherein the biological output, behavioral output, or environmental output comprises real-time data.

16. The processing system of claim 14, wherein the alert comprises a recommendation to take a medication or to not take a medication.

17. The processing system of claim 14, wherein the alert comprises an observed side effect notification.

18. The processing system of claim 17, wherein the processor is further configured to receive a medical history of the patient.

* * * * *